United States Patent [19]

Schramm et al.

[11] Patent Number: 5,674,979
[45] Date of Patent: Oct. 7, 1997

[54] AGENT FOR INHIBITING SYMMETRICAL PROTEINS, IN PARTICULAR ENZYMES

[76] Inventors: Wolfgang Schramm, Medizinische Kliniken Innenstadt der Universitat Munchen Zienssenstr. 1, 8000 Munchen 2; Hans J. Schramm, Max-Planck-Institut für Biochemie Am Klopferspitz, 8033 Martinsried, both of Germany

[21] Appl. No.: 584,579

[22] Filed: Jan. 11, 1996

Related U.S. Application Data

[60] Continuation of Ser. No. 332,447, Oct. 31, 1994, abandoned, which is a division of Ser. No. 112,215, Aug. 26, 1993, abandoned, which is a continuation of Ser. No. 976,003, Nov. 13, 1992, abandoned, which is a continuation of Ser. No. 585,141, Dec. 7, 1990, abandoned.

[30] Foreign Application Priority Data

Feb. 10, 1989 [DE] Germany .......................... 39 04 040.2

[51] Int. Cl.$^6$ .............................. A61K 38/00; C07K 5/00; C07K 7/00
[52] U.S. Cl. .......................... 530/326; 530/327; 530/328; 530/329; 530/330
[58] Field of Search .................... 530/326, 327, 530/328, 329, 330

[56] References Cited

FOREIGN PATENT DOCUMENTS 0077028  10/1982  European Pat. Off. .
0352000   7/1989  European Pat. Off. .

OTHER PUBLICATIONS

Pechik et al., FEBS LETT., vol. 247, No. 1, pp. 118–122, Apr. 1989.
Billish, S. et al., J. Biol. Chem. 263:17905–17908 (1988).

Primary Examiner—Avis M. Davenport
Attorney, Agent, or Firm—Venable, Baetjer, Howard & Civiletti, LLP

[57] ABSTRACT

The invention relates to substances for the inhibition of symmetric proteins, in particular enzymes, in particular the inhibition of HIV protease, in the form of structurally symmetric or near symmetric enzyme inhibitors, chazacterized by the same symmetry, or approximate or piecewise (yet sufficient for inhibition) symmetry, as the enzyme molecule to be inhibited.

4 Claims, No Drawings

SEQUENCE LISTING ( 1 ) GENERAL INFORMATION:

( i i i ) NUMBER OF SEQUENCES: 20

( 2 ) INFORMATION FOR SEQ ID NO:1:

( i ) SEQUENCE CHARACTERISTICS:
( A ) LENGTH: 6 amino acids
( B ) TYPE: amino acid
( D ) TOPOLOGY: linear ( i i ) MOLECULE TYPE: peptide ( i i i ) HYPOTHETICAL: YES ( x i ) SEQUENCE DESCRIPTION: SEQ ID NO:1:

Gly Ala Phe Pro Ile Ala
1               5

( 2 ) INFORMATION FOR SEQ ID NO:2:

( i ) SEQUENCE CHARACTERISTICS:
( A ) LENGTH: 4 amino acids
( B ) TYPE: amino acid
( D ) TOPOLOGY: linear ( i i ) MOLECULE TYPE: peptide ( i i i ) HYPOTHETICAL: YES ( x i ) SEQUENCE DESCRIPTION: SEQ ID NO:2:

Arg Ala Asn Leu
1

( 2 ) INFORMATION FOR SEQ ID NO:3:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( i i i ) HYPOTHETICAL: YES ( x i ) SEQUENCE DESCRIPTION: SEQ ID NO:3:

Ile Asp Thr Gly Ala
1                5

( 2 ) INFORMATION FOR SEQ ID NO:4:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( i i i ) HYPOTHETICAL: YES ( x i ) SEQUENCE DESCRIPTION: SEQ ID NO:4:

Ile Asp Ser Gly Ala
1                5

( 2 ) INFORMATION FOR SEQ ID NO:5:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( i i i ) HYPOTHETICAL: YES ( x i ) SEQUENCE DESCRIPTION: SEQ ID NO:5:

Asp Thr Gly Ala
1

( 2 ) INFORMATION FOR SEQ ID NO:6:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( i i i ) HYPOTHETICAL: YES ( x i ) SEQUENCE DESCRIPTION: SEQ ID NO:6:

Ile Gly Arg Asn
1

( 2 ) INFORMATION FOR SEQ ID NO:7:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( i i i ) HYPOTHETICAL: YES ( x i ) SEQUENCE DESCRIPTION: SEQ ID NO:7:

```
Ile Gly Gly Arg Asn
1               5
```

( 2 ) INFORMATION FOR SEQ ID NO:8:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( i i i ) HYPOTHETICAL: YES ( x i ) SEQUENCE DESCRIPTION: SEQ ID NO:8:

```
Thr Leu Trp Gln Arg Pro Leu Val
1               5
```

( 2 ) INFORMATION FOR SEQ ID NO:9:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( i i i ) HYPOTHETICAL: YES ( x i ) SEQUENCE DESCRIPTION: SEQ ID NO:9:

```
Leu Trp Gln Arg Pro Leu
1               5
```

( 2 ) INFORMATION FOR SEQ ID NO:10:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( i i i ) HYPOTHETICAL: YES ( x i ) SEQUENCE DESCRIPTION: SEQ ID NO:10:

```
Trp Gln Arg Pro
1
```

( 2 ) INFORMATION FOR SEQ ID NO:11:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( i i i ) HYPOTHETICAL: YES ( x i ) SEQUENCE DESCRIPTION: SEQ ID NO:11:

```
Leu Trp Gln Arg Pro
1               5
```

( 2 ) INFORMATION FOR SEQ ID NO:12:

( i ) SEQUENCE CHARACTERISTICS:
  ( A ) LENGTH: 4 amino acids
  ( B ) TYPE: amino acid
  ( D ) TOPOLOGY: linear ( i i ) MOLECULE TYPE: peptide ( i i i ) HYPOTHETICAL: YES ( x i ) SEQUENCE DESCRIPTION: SEQ ID NO:12:

Ser Glu Asn Tyr
1

( 2 ) INFORMATION FOR SEQ ID NO:13:

( i ) SEQUENCE CHARACTERISTICS:
    ( A ) LENGTH: 4 amino acids
    ( B ) TYPE: amino acid
    ( D ) TOPOLOGY: linear ( i i ) MOLECULE TYPE: peptide ( i i i ) HYPOTHETICAL: YES ( x i ) SEQUENCE DESCRIPTION: SEQ ID NO:13:

His Pro His Tyr
1

( 2 ) INFORMATION FOR SEQ ID NO:14:

( i ) SEQUENCE CHARACTERISTICS:
    ( A ) LENGTH: 4 amino acids
    ( B ) TYPE: amino acid
    ( D ) TOPOLOGY: linear ( i i ) MOLECULE TYPE: peptide ( i i i ) HYPOTHETICAL: YES ( x i ) SEQUENCE DESCRIPTION: SEQ ID NO:14:

Arg Ser Gln His
1

( 2 ) INFORMATION FOR SEQ ID NO:15:

( i ) SEQUENCE CHARACTERISTICS:
    ( A ) LENGTH: 4 amino acids
    ( B ) TYPE: amino acid
    ( D ) TOPOLOGY: linear ( i i ) MOLECULE TYPE: peptide ( i i i ) HYPOTHETICAL: YES ( x i ) SEQUENCE DESCRIPTION: SEQ ID NO:15:

Arg Ser Gln Asn
1

( 2 ) INFORMATION FOR SEQ ID NO:16:

( i ) SEQUENCE CHARACTERISTICS:
    ( A ) LENGTH: 5 amino acids
    ( B ) TYPE: amino acid
    ( D ) TOPOLOGY: linear ( i i ) MOLECULE TYPE: peptide ( i i i ) HYPOTHETICAL: YES ( x i ) SEQUENCE DESCRIPTION: SEQ ID NO:16:

His Pro Phe His Leu (2) INFORMATION FOR SEQ ID NO:17:

(i) SEQUENCE CHARACTERISTICS:
        (A) LENGTH: 16 amino acids
        (B) TYPE: amino acid
        (D) TOPOLOGY: linear (ii) MOLECULE TYPE: peptide (iii) HYPOTHETICAL: YES (xi) SEQUENCE DESCRIPTION: SEQ ID NO:17:

Trp Lys Pro Lys Met Ile Gly Gly Ile Gly Gly Phe Ile Lys Val Arg
    1             5                     10                 15

(2) INFORMATION FOR SEQ ID NO:18:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (iii) HYPOTHETICAL: YES (xi) SEQUENCE DESCRIPTION: SEQ ID NO:18:

Gln Ile Leu Ile Glu Cys
    1             5

(2) INFORMATION FOR SEQ ID NO:19:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (iii) HYPOTHETICAL: YES (xi) SEQUENCE DESCRIPTION: SEQ ID NO:19:

Val Gly Pro Thr Pro Val Asn
    1             5

(2) INFORMATION FOR SEQ ID NO:20:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (iii) HYPOTHETICAL: YES (xi) SEQUENCE DESCRIPTION: SEQ ID NO:20:

Ala Gly Arg Asn Leu Leu Thr Gln Ile
    1             5

AGENT FOR INHIBITING SYMMETRICAL PROTEINS, IN PARTICULAR ENZYMES

This application is a continuation of application Ser. No. 08/332,447, filed 31 Oct. 1994, now abandoned, which is a divisional of application Ser. No. 08/112,215, filed 26 Aug. 1993, now abandoned, which is a continuation of application Ser. No. 07/976,003, filed 13 Nov. 1992, now abandoned, which is a continuation of application Ser. No. 07/585,141, filed 7 Dec. 1990, now abandoned.

The invention relates to substances for the inhibition of symmetric enzymes, in particular for the inhibition of HIV-proteinase or protease, in the form of structurally symmetric or approximately or piecewise symmetric enzyme inhibitors.

The specific inhibition of foreign enzymes (from pathogenic bacteria or viruses) or native enzymes in pathological states is an important concern of medicine, allowing a careful therapy against various diseases. The invention is a result of a search for such specific inhibitors against the immunodeficiency disease AIDS (Acquired Immuno Deficiency Syndrome). This indicated targetting the proteinase, hereinafter termed 'protease' for short, from HIV (Human Immunodeficiency Virus). This enzyme is responsible for processing precursor proteins, whose cleavage results in the mature virus protein, from which the complete virus may be assembled. A specific inhibitor against HIV protease should prevent proliferation of the virus and relieve the symptoms of the disease. Such a strategy of protease inhibition is particularly welcome for AIDS, in that inhibition of the immune system carries the risk of destroying the remaining immunity, whilst therapy using existing inhibitors of HIV reverse transcriptase (eg AZT, FLT, suramin) suffers from severe side effects. In addition, AIDS therapy using other compounds (eg polysulphated polysaccharrides) has not yet been demonstrated convincingly, or is also burdened by severe side effects.

A considerable volume of literature exists on the HIV protease—some relevant references are:

L. H. Pearl and W. R. Taylor, Nature (1987) 329, 351–354

I. Katoh et al., Nature (1987) 329, 654–656

C. Debouck et al., P.N.A.S. (1987) 84, 8903–8906

P. L. Darke et al., B. B. Res. Comm. (1988) 156, 297–303

S. F. J. Le Grice et al., EMBO J. (1988) 7, 2547–2553

M. C. Graves et al., P.N.A.S. (1988) 85, 2499–2453

M. Kotler et al., P.N.A.S. (1988) 85, 4185–4189

S. Billich et al., J.B.C. (1988) 263, 17905–17908

S. Seelmeier et al., P.N.A.S. (1988) 85, 6612–6616

E. P. Lillehoj et al., J. Virol. (1988) 62, 3053–3058

L. E. Henderson et al., J. Virol. (1988) 62, 2587–2595

H.-G. Kraeusslich et al., J. Virol. (1988) 62, 4393–4397

M. Miller et al., J. Mol. Biol. (1988) 204, 211–212

The invention rests on obtaining an effective influence on proteases (through the corresponding proteins), in order to achieve a more effective therapy for AIDS and other diseases involving enzymes. Guiding factors hereby are high specificity and favourable therapeutic index.

This task is achieved by enzyme inhibitors whose molecular structure bears the same or approximate or piecewise symmetry as that of the enzyme molecule to be inhibited.

Such enzyme inhibitors are tailored such that their symmetry matches that of a target enzyme essential for the advance of the disease. These inhibitors can be synthesised using established methods and administered in the usual ways, eg i.v. or orally, so that enzyme inhibition through these compounds represents a practical therapy.

It has been shown that symmetrically built ('symmetric' for short) enzyme inhibitors are particularly suited to inhibition of HIV proliferation, through inhibition of the symmetric (consisting of two identical half molecules) virus encoded protease. It is further known that other likewise symmetric enzymes can be inhibited in this way. Although symmetric or piecewise symmetric enzyme inhibitors are known (eg for a reverse transcriptase whose structure and symmetry are as yet unknown), the present principle of action through correspondence of the enzyme and inhibitor symmetries has not yet been described. Symmetric peptide based inhibitors have as far as is known not yet been described, and could not be expected as natural enzyme substrates (even of those that are symmetric) are never symmetric. The invention is based on the realisation that in such reactions (binding of an asymmetric substrate to a symmetric enzyme or inhibition of a symmetric enzyme by asymmetric enzyme inhibitors), either only one (well fitting) half of the peptide is responsible for the binding, with the other half playing a subsidiary role, or neither half fit optimally but together give sufficient affinity for inhibition. On the other hand, well fitting symmetric peptides and peptide derivatives (or other symmetric organo chemical compounds) should produce a stronger binding to (and hence inhibition of) symmetric enzymes.

It is further recognised that enzyme complexes—symmetric or asymmetric—composed of subunits can be inhibited if the interactions holding the subunits together are disrupted by suitable compounds, such that either a total or partial decomposition or instability of the complex is achieved, which would totally or partially disrupt the formation of the complex or the correct spatial structure or conformation necessary for the enzymatic reaction. This can be achieved through the selection of peptides or peptide-like compounds or other organo-chemical compounds containing the amino acid sequence, or derivatives thereof or related thereto, that are responsible for the integrity of the functional tertiary and quaternary structure in the native enzyme.

This latter approach is particularly valid in relation to the enzyme complex active site, where relatively small perturbations can effect an inactivation of the enzyme. Peptides containing sequences which form or stabilise the active site (or compounds of similar structure) are therefore particularly suited to inhibiting enzyme activity, in that they perturb the structure or prevent the correct spatial structure from being formed. The compounds advocated here need not themselves be symmetric, however the interaction is especially effective for symmetric enzymes, where more identical binding sites are available and the interaction thereby amplified by the number of subunits. This principle holds also for asymmetric proteins composed of subunits.

The advantages gained are a very specific inhibition of proteins (enzymes, proteases) through consideration of the detailed structural properties of the target protein, and the increased binding of the inhibitor substance through use of the symmetry properties, whereby at least twice the binding area is utilised.

The high specificity and binding potential of these inhibitors should allow a relatively careful treatment of AIDS, as well as other diseases. Such treatment is particularly necessary in the case of AIDS, as the immune system is damaged by the disease and therefore the susceptibility of the body to any disease is drastically increased. In addition, as the virus nucleic acid is incorporated into the genome, AIDS cannot be cured causally, and so a lifelong and therefore very considerate and specific therapy is required.

One such substance that particularly distinguishes itself is one in which the peptide or peptide-like structure or other organo-chemical compound possesses a central organo-chemical group, for simplicity termed M, to which are bound residues X, Y, Z, U, R as side chains, which can be organic residues, in particular amino acids or their derivatives or monosaccharides or their derivatives or fatty acids or their derivatives, in particular however peptides, that are the same or approximately the same and are symmetric or approximately symmetric with regard to the group M, giving rise to an overall symmetric or approximately or piecewise symmetric total compound. The term 'symmetry' is used here in the usual stereo chemical sense, with regards to proteins always a rotation axis.

Such inhibitor substances can therefore be used to inhibit proteins, in particular enzymes, if they at least possess a local symmetry corresponding to the part of the molecule to be inhibited. These are for example enzymes that are wholly or in part composed of equal subunits, although they may possess additional subunits. Apart from HIV protease, from which this is known, there are other vital proteins, membrane proteins, cytokines, restriction enzymes and multi-enzyme complexes whose symmetries are either known or can be determined sufficiently.

The symmetric inhibitors for symmetric proteins possess the same symmetry as that of the protein to be inhibited, and consist as mentioned of a central group M and side arms, denoted simply X for the sake of clarity in the present discussion, resulting in the formula $$M\,(X)_n$$

where the symmetry of the protein is n-fold, eg '2' for proteins with a twofold axis, symmetry C2.

As mentioned, the side arms can be composed of amino acids or derivatives or other organo-chemical compounds, however peptides are more advantageous as they can be synthesised easily and in part automatically. In principle, however, sidearms composed of fatty acids, carbohydrates, or even inorganic compounds are possible, if suitable for a particular enzyme. The use of small peptides is especially preferred, usually between 2 and 4 amino acids per sidearm.

The two or more arms must be symmetric or approximately or piecewise symmetric to each other, in the sense that the symmetry of the protein to be inhibited, eg a twofold axis, is also found in the inhibitor. In the case of a dyad, a rotation of the inhibitor around the twofold axis must superimpose one side chain on the other.

This can be achieved for example in the following ways:

(a) if the direction of the peptide chain is different in each part, such that in one half the NH—CO vector points towards the centre, whilst that in the other half points away from the centre, then the two halves must be composed of amino acids of opposite chirality (D instead of L and vice versa) to achieve compatibility. The resulting inhibitor is then approximately symmetric with respect to its side chains, but not in relation to the peptide bonds. In general, however, this is enough as the inhibitor is sufficiently symmetric for inhibition of the enzyme.

(b) if not all the amino acids or other residues of the inhibitor are symmetric (eg a tyrosine on one side complemented by a phenylalanine), but the remaining amino acids are equal and complementary, then the compound can still produce a high inhibitory activity. Such inhibitory substances can show more favourable properties than strictly symmetric compounds with respect to solubility, membrane accessibility etc. Structural and physico-chemical parameters such as size, charge, hydrophilicity and the like determine the variation. Thus the inhibitor Phe-Thr-Ile-M-Leu-Ser-Tyr is 'more symmetric' with respect to the mentioned properties than Ala-Arg-Gly-M-Gly-Asp-Ala (unequal charge, Arg/Asp)

or

Gly-Gly-Trp-M-Gly-Gly-Gly (unequal size, Trp/Gly)

as the difference between eg Thr and Ser is less than that between Arg and Asp or Trp and Gly.

Small deviations from symmetry can in principle be advantageous; the gain in affinity through optimal structural fit (by symmetry fit) must simply be large enough for tight binding.

The central groups have the tasks of (a) transferring the symmetry of the protein to the inhibitor compound (b) holding the side arms responsible for a favourable binding at the right distance and angle, and (c) themselves fitting well to the protein, eg at the active site of an enzyme, for a favourable binding of the inhibitor and thus contributing to the protein inhibition.

The central groups themselves must not necessarily be symmetric, for example if the sidearms are largely responsible for the affinity. The central groups can be chiral, eg statin. It is only important that the correct orientation of the side arms is imparted, and that the distance is optimal. This should pose no problem for a preparative chemist with a knowledge of the symmetry or perhaps even the exact structure of the enzyme. The size of the central group can vary, as with its chemical nature, so that inorganic groups like —P(O)OH— or even a bond itself can serve as central groups. A structural mimicry of the substrate or of a transition state in the enzymatic reaction by the inhibitor can be important.

Central groups which, although possessing the correct side chains (appropriate order and chirality of the amino acids) maintained at the correct distance, have incorrectly placed side chains with respect to the direction of the symmetry axis are unsuitable, eg if 'up' and 'down' are exchanged:

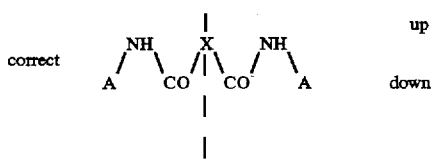

-continued

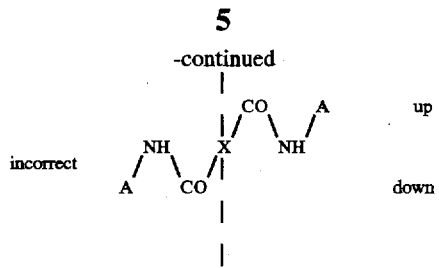
The following examples demonstrate piecewise or approximately symmetric peptides that inhibit HI-virus in H9 cells.
EXAMPLE 1

A) H-(D)-Asn-(D)-Leu-(D)-Thr-Gly-OH

B) t-BOC-L-Leu-NH—$CH_2$—CHOH—$CH_2$—COOH

C) Cl—$CH_2$—CO-Gly-Ala-Phe-Pro-Ile-Ala-OH (Cl—$CH_2$—CO-SEQ ID NO: 1-OH)

D) $CH_3$CO-Thr-Leu-Asn-NH—$CH_2$—CHOH—$CH_2$—NH-Asn-Leu-Thr-$COCH_3$

E) Ala-Asp-Thr-β-napthylamide

Compounds (a), (b), (c), (d) were tested in the molarity range from 0.1 μM to 1000 μM. Infectivity tests were carried out as follows: an HIV-1 suspension containing $10^2$ infectious units was absorbed on to $5\times10^6$ H9 cells in a volume of 1 ml for 2 hours at 4° C. After this time, 9 ml of tissue culture medium with the required inhibitor concentration was added. The medium was exchanged with fresh medium plus inhibitor daily. Two control cultures were also prepared, one without inhibitor to determine the normal virus replication rate, the other containing inhibitor but no virus, to determine whether the substances were cytotoxic for H9 cells. Judged by colouration of the cells with trypan blue, no cytotoxic effect was observed. The amount of virus antigen produced by the infected cells was measured daily using Elisa for eight days, indicating the amount of HIV-1 antigen in the tissue culture medium. After this, the cells were pelleted, washed in medium without inhibitor, and further incubated in inhibitor-less medium. The antigen production was measured on days 9 and 12 (ie 1 and 3 days after removal of the inhibitor). Virus production was also measured on days 7, 8, 9, and 12 by determining the amount of reverse transcriptase in the supernatant of the cell medium.

A clear inhibition of HIV-1 replication by compounds (a) to (d) resulted, as shown in the accompanying tables I and II.

In the following examples, R and R' indicate peptide residues, preferrably up to 9 amino acids maximally, especially with 2 to 4 amino acids, or other short chemical residues, eg $CH_3(CH_2)_nCO$— with n=1 to 10, $CH_3CO$—, H—, —$NH_2$, —NHR, —OR; X indicates small amino acid residues such as Gly, Ala, Ser or other small residues, A and B are amino acids or other organic residues. This holds for all the following examples unless otherwise stated.

EXAMPLE 2

R-(D)-Ser-(D)-Gln-(D)-Leu-(D)-Phe-(D)-Asn-(D)-Gln-OR'

Acetyl-(D)-Asp-(D)-Leu-(O)-Phe-(D)-Leu-(D)-Ile-(D)-Lys-$NH_2$

Acetyl-(D)-Ala-(D)-Val-(D)-Pro-(D)-Phe-(D)-Asn-(D)-Arg-$NH_2$

Acetyl-(D)-Gln-(D)-Val-(D)-Ile-(D)-Pro-(D)-Tyr-(D)-Asn-(D)-Gln-(D)-Arg-$NH_2$

By their otherwise substrate like structure, such substances can place a non- or slow-cleaving bond (is reversed polarity) at the clearable —CONH— peptide bond position, eg via the retro-inverse principle of simultaneous reversal of sequence direction and amino acid chirality, eg using the formula (D)-A-NHCO-(D)-B-NHCO-(D)-C-NHCO-(D)-D- in place of the natural peptide substrate of formula (L)-A-CONH-(L)-B-CONH-(L)-C-CONH-(L)-D- whereby pairs D and A and C and B are symmetric or exhibit at least a structural similarity regarding hydrophobicity, charge, side chain size etc.

EXAMPLE 3

Acetyl-(D)-Arg-(D)-Ala-(D)-Gln-(D)-Leu-NH—CO—CH($C_4H_9$)—CO-(L)-Gln-(L)-Ala-(L)-Arg-$NH_2$ Acetyl-(L)-Arg-(L)-Ala-(L)-Asn-(L)-Leu-NH—$CH_2$—CH($C_3H_7$ )—CO-(D)-Asn-(D)-Gln-(D)-Leu-$NH_2$ (Acetyl-SEQ ID NO: 2-NH)

Acetyl-(D)-Arg-(D)-Ala-(D)-Gln-NH—$CH_2$—CO-(L)-Gln-(L)-Ala-(L)-Arg-$NH_2$

Acetyl-(D)-Arg-(D)-Ala-(D)-Asn-statin-(L)-Asn-(L)-Ala-(L)-Arg-$NH_2$

Acetyl-(L)-Arg-(L)-Ala-(L)-Gln-statin-(D)-Gln-(D)-Ala-(D)-Arg-OH

Fluoroacetyl-(L)-Arg-(L)-Ala-(L)-Asn-(L)-statin-(D)-Asn-(D)-Ala-(D)-Arg-$NH_2$

Acetyl-(D)-Arg-(D)-Ala-(D)-Leu-statin-(L)-Leu-(L)-Ala-(L)-Arg-$NH_2$

Acetyl-(D)-Leu-(D)-Arg-(D)-NH—$CH_2$—CH(OH)—$CH_2$—CO-(L)-Asn-(L)-Arg-(L)-Leu-$NH_2$ In these compounds, one half of the peptide chain is composed of amino acid residues of one chirality whilst those in the other half exhibit the opposite chirality, such that an overall symmetric or approximate or piecewise symmetric total compound results, eg the formulae (L)-C-(L)-B-(L)-A-(D)-A-(D)-B-(D)-C or (D)-C-(D)-B-(D)-A-(L)-A-(L)-B-(L)-C exhibit the expressed principle, where A, B and C represent amino acid residues. It should be noted that insertion of a suitable central group requires consideration of the principle stated on page 5.

The inhibitor achieves inhibition of the protease through placing an uncleavable bond in the inhibitor at the site of the clearable peptide bond, as explained in example 7, and that the required compounds can have two statin residues or two related compounds bound to an asymmetric central organo-chemical group in such a way as to form an overall spatially symmetric or approximately or piecewise symmetric total compound, as explained in example 4, and that the compounds have two peptides or peptide like compounds, with equal or approximately equal and corresponding amino acid sequence and equal chirality but with opposite peptide bond directions, bound to a central organo-chemical group with two equal substituents in such a way that an overall spatially symmetric or approximately or piecewise symmetric total compound arises, as shown in example 7, further, as shown also in example 8, that the compounds can have two peptides or peptide like compounds, with equal or approximately equal and corresponding amino acid sequences with the same peptide bond direction but with opposite amino acid chirality, bound to a central organo-chemical group with two different substituents in such a way as to form an overall symmetric or approximately symmetric or piecewise symmetric compound, and finally, that the compounds can have chemically reactive residues, eg corresponding to the formulae XCH$_2$CO—, N$_2$CHCO—, NC—CH$_2$—CO—, RO$_2$C—, CH$_2$=CR—, RO$_n$S—, HS—, RO(H$_2$N=)C$^+$—, so bound to the symmetric or approximately symmetric or piecewise symmetric compound that the compound can become reversibly or irreversibly bound to the target enzyme. Here X means halogen, R is an ester residue with 1 to 12 carbon atoms, but preferrably a C$_1$–C$_3$ residue, or a phenyl or benzyl residue, and n=1 to 3.

EXAMPLE 4

R-statin-X-statin-R' or

CH$_3$CO-statin-X-statin-NH$_2$ or

Isovaleryl-Ser-Ser-statin-Ala-statin-NH$_2$ or

Acetyl-Ser-statin-Gly-statin-NH$_2$ or

Acetyl-statin-Ala-statin-NH$_2$ or

Fluoroacetyl-statin-Ala-statin-NH$_2$ or

Acetyl-statin-Ala-statin-NH—CO—CH$_2$—CN;

further: combinations of (3S,4S)-, (3R,4R)-, (3R,4S)- and (3S,4R)-statin in an above or similar manner;

further: modification of R corresponding to the sequence of pepstatin A, typical binding sequences of typical substrates of HIV-protease, etc.

In the above compounds, two statin residues or related compounds are bound to an asymmetric central organo-chemical group so as to form an overall symmetric or approximately or piecewise symmetric compound.

EXAMPLE 5

R-Asp-Thr-Gly-R' or

R-Asp-Ser-Gly-R' or

R-A-Asp-Thr-Gly-B-R' or

Acetyl-Ile-Asp-Thr-Gly-Ala-NH$_2$ (Acetyl-SEQ ID NO: 3-NH$_2$) or

Isovaleryl-Ile-Asp-Ser-Gly-Ala-NH—(CH$_2$)3—CH$_3$ (Isovalery-SEQ ID NO: 4-NH(CH$_2$)$_3$—CH$_3$) or Acetyl-Asp-Thr-Gly-Ala-NH$_2$ (Acetyl-SEQ ID NO: 5-NH$_2$)

Chloracetyl-Asp-Thr-Gly-Ala-NH$_2$ (Chloracetyl-SEQ ID NO: 5-NH$_2$)

Acetyl-Ile-Gly-Arg-Asn-NH$_2$ (Acetyl-SEQ ID NO: 6-NH$_2$)

Acetyl-Ile-Gly-Gly-Arg-Asn-Ile-NH$_2$ (Acetyl-SEQ ID NO: 7-NH$_2$)

The compounds given contain the amino acid sequence Asp-Thr-Gly or Asp-Ser-Gly, or related or similar amino acid sequences or structurally similar organo-chemical compounds, that in the target enzyme contribute to or are responsible for a correct formation of a functional active site from identical or corresponding parts of different subunits of the enzyme complex, such that the compounds can impair the structure or the stability of the active site or prevent its formation.

EXAMPLE 6

Acetyl-Thr-Leu-Trp-Gln-Arg-Pro-Leu-Val-NH$_2$ (Acetyl-SEQ (ID NO: 8-NH$_2$) or

Fluoroacetyl-Leu-Trp-Gln-Arg-Pro-Leu-NH$_2$ (Fluoroacetyl-SEQ ID NO: 9-NH$_2$) or Isovaleryl-Trp-Gln-Arg-Pro-NH$_2$ (Isovaleryl-SEQ ID NO: 10-NH$_2$) or H-Leu-Trp-Gln-Arg-Pro-NH$_2$ (H-SEQ ID NO: 11-NH$_2$) or similar compounds These compounds contain, in the case of HIV protease as target enzyme, the amino acid sequence Thr-Leu-Trp-Gln-Arg-Pro-Leu-Val or related or similar amino acid sequences or structurally similar organo-chemical residues or parts thereof, responsible for the association of the HIV protease, and for the formation or integrity of the functional enzyme complex, so that the given compounds can disrupt the structure or stability of the enzyme complex or reduce its enzymatic activity or prevent its formation.

EXAMPLE 7

Acetyl-Arg-Leu-Asn-NH—(CH$_2$)3—NH-Asn-Leu-Arg-Acetyl

Acetyl-Arg-Leu-Asn-NH—CH$_2$—O—CH$_2$—NH-Asn-Leu-Arg-Acetyl

Acetyl-Arg-Leu-Asn-NH—CH$_2$—CHOH—CH$_2$—NH-Asn-Leu-Arg-Acetyl

Acetyl-Arg-Leu-Asn-NH—CH$_2$—NH—CH$_2$—NCH$_3$-Asn-Leu-Arg-Acetyl

H-(D)-Leu-(D)-Leu-(D)-Asn-NH—CHF—CO—CHF—NH-(D)-Asn-(D)-Leu-(D)-Arg-H

In the case of proteases as target enzymes, enzyme inhibition with the given compounds is achieved through the presence of an uncleavable bond in place of the clearable peptide bond, eg one of the formulae —S—S—, —S—, —O—, —CO—CHR—CH(OH)—CHR'—CO—, —NR—NR'—, —NH—CHR—CH(OH)—CHR'—NH—, —NH—CF$_2$—CO—CH$_2$NH—, —NH—CF$_2$CO—CF$_2$—NH—, —CO—(CH$_2$)$_3$—CO—, —NH—(CH$_2$)$_3$—NH—, —CO—CH$_2$—O—CH$_2$—CO—, —N(OR)—, —NR—, —P(O)$_n$OH—, —CO—CHR—CO—, —NH—CH$_2$—O—CH$_2$—NH—, —CO—CH$_2$—NR—CH$_2$—CO—, —N(C$_5$H$_1$1)—CF$_2$—CO—CF$_2$—N(C$_5$H$_{11}$)—, N(C$_4$H$_9$)—CH$_2$—CH(OH)—CH$_2$—N(C$_4$H$_9$)—, (2S,3S)—NH—CH(CH$_2$C$_6$H$_{11}$)—CH(OH)—CH$_2$—NR—, or similar compounds, whereby R and R' signify hydrogen or aryl or alkyl residues up to C$_{12}$ and n=1 or 2.

In the given compounds, two peptides or peptide like compounds with equivalent or near equivalent or complementary amino acid sequences and like chiralities, but opposite directions, can be so bound to a central organo-chemical group with two equal substituents to form an overall spatially symmetric or approximately or piecewise symmetric compound, eg corresponding to the formulae (L)-A-CONH-(L)-B-CONH-(L)-C-CONH-M-NHCO-(L)-C-NHCO-(L)-B-NHCO-(L)-A or (L)-C-NHCO-(L)-B-NHCO-(L)-A-NHCO-M-CONH-(L)-A-CONH-(L)-B-CONH-(L)-C or (L)-A-CONH-(L)-B-CONH-(L)-C-CONH-NHCO-(L)-C-NHCO-(L)-B-NHCO-(L)-A or (L)-C-NHCO-(L)-B-NHCO-(L)-A-NHCO-CONH-(L)-A-CONH-(L)-B-CONH-(L)-C or (L)-A-CONH-(D)-B-CONH-(L)-C-CONH-M-NHCO-(L)-C-NHCO-(L)-B-NHCO-(L)-A or (L)-C-NHCO-(L)-B-NHCO-(L)-A-NHCO-M-CONH-(L)-A-CONH-(L)-B-CONH-(D)-C or (L)-B-CONH-(L)-B-CONH-(L)-C-CONH-M-NHCO-(L)-C-NHCO-(L)-B-NHCO-(L)-A or (L)-B-NHCO-(L)-A-NHCO-M-CONH-(L)-A-CONH-(L)-B-CONH-(L)-C, whereby A, B, C represent amino acid residues and M and organo-chemical group (see above for examples).

EXAMPLE 8

Acetyl-(L)-Arg-(L)-Leu-(L)-Asn-NH—(CH$_2$)3—CO-(D)-Asn-(D)-Leu-(D)-Arg-NH$_2$

Acetyl-(L)-Arg-(L)-Leu-(L)-Asn-NH—CH$_2$—CHOH—CH$_2$—CO-(D)-Asn-(D)-Leu-(D)-Arg-NH$_2$ H-(L)-Leu-(L)-Asn-NH—CH$_2$—CO—CF$_2$—CO-(D)-Asn-(D)-Leu-(D)-Arg-NH$_2$ H-Val-Tyr-[CH$_2$—NH]—CH$_2$—[CH$_2$—NH]-(D)-Tyr-(D)-Val-OCH$_3$ (reduced -Tyr-Gly-D-Tyr-)

Additional to the examples given above in example 7, these compounds possess a central organo-chemical group with two different substituents, bound to which are two peptides or peptide like compounds with equivalent or approximately equivalent or complementary amino acid sequences, with opposite directions and chiralities of the amino acids, but the same direction of the peptide bonds, in such a way that an overall spatially symmetric or approximately or piecewise symmetric compound arises, eg corresponding to the formulae (L)-A-CONH-(L)-B-CONH-(L)-C-CONH-M-CONH-(D)-C-CONH-(D)-B-CONH-(D)-A or (L)-A-CONH-(D)-B-CONH-(L)-C-CONH-M-CONH-(D)-C-CONH-(D)-B-CONH-(D)-A or (D)-A-CONH-(D)-B-CONH-(D)-C-CONH-M-CONH-(L)-C-CONH-(L)-B-CONH-(L)-A or (D)-A-NHCO-(D)-B-NHCO-(D)-C-NHCO-M-NHCO-(L)-C-NHCO-(L)-B-NHCO-(D)-A whereby A, B, C represent amino acid residues and M a central group.

In the case of proteases as target enzymes, inhibition is achieved with these compounds by plating a non-clearable bond at the site of the cleavable peptide bond, eg of the formula —CR$_2$—NH—, —CH(OH)—NH—, —CO—N(CH$_3$)—, —P(O)$_n$—NH—, -(3S,4S)-4-amino-3-hydroxy-6-methylheptanoic acid-(statin), -(3S ,4S)-3-hydroxy-4-amino-5-phenylpentanoic acid- (AHPPA), or similar compounds, whereby R and R' represent hydrogen or aryl or alkyl residues up to C$_{12}$ and n=1 or 2.

EXAMPLE 9

NH$_2$-Arg-Leu-Asn-CO—(CH$_3$)$_3$—CO-Asn-Leu-Lys-NH$_2$

H$_2$N-(D)-Leu-(D)-Ash-CO—(CH$_2$)$_3$—CO-(D)-Asn-(D)-Ile-NH$_2$

NH$_2$-Leu-Asn-CO—CH$_2$—NH—CH$_2$—CO-Asn-Leu-Arg-OR

NH$_2$-Arg-Leu-Asn-CO—CH$_2$—CHOH—CH$_2$—CO-Ash-Leu-Arg-NH$_2$

Acetyl-Arg-Leu-Asn-NH—CH$_2$—NH—CH$_2$—NH-Asn-Leu-Arg-Acetyl

H-Leu-Leu-Asn-NH—CHF—CO—CHF—NH-Asn-Leu-Arg-H

Acetyl-Arg-Leu-Asn-NH—CH$_2$—O—CH$_2$—NH-Asn-Leu-Arg-Acetyl

Acetyl-Arg-Leu-Asn-NH—CH$_2$—CH(OH)—CH$_2$—NH-Asn-Leu-H

H-(L)-Arg-(L)-Ile-(L)-Asn-NH—CH$_2$—CO-(D)-Gln-(D)-Leu-(D)-Arg-OH

H-Ala-Ala-statin-(D)-Val-(D)-Val-OCH$_3$

Additional to those given in the two previous examples, these compounds display a central organo-chemical group to which are attached two peptides or peptide like compounds with different amino acid sequences, but with a similar distribution of corresponding residues of equal electrical charge or equal or similar hydrophobicity or hydrophilicity or side chain size or other physico-chemical property such that an overall approximately or piecewise spatially symmetric compound results, eg corresponding to the following formulae:

(L)-C-(L)-A$^+$—CONH—M—CONH-(D)-B$^+$-(D)-C, or (L)-C-(L)-A$^+$—CONH—M—NHCO-(L)-B$^+$-(L)-C, or (L)-C-(L)-A$^+$—CONH—M—CONH-(D)-B$^+$-(D)-D, or (L)-C-(L)-A$^+$—CONH—M—CONH-(D)-B$^+$-(L)-C, or (L)-D-(L)-AX—CONH—M—NHCO-(L)-BX-(L)-C, or (L)-C-(L)-AX—CONH—M—CONH-(D)-BX-(D)-C, or (L)-C-(L)-AX—CONH—NHCO-(L)-BX-(L)-C, or (L)-C-(L)-A$^+$—HNCO—CONH-(D)-B$^+$-(D)-D, where A$^+$, B$^+$ represent two different amino acids with the same charge, M a central organo-chemical group and AX, BX two different amino acids with comparably sized hydrophobic or hydrophilic sidechains.

Finally, some examples for central groups (M), for side chains and for complete inhibitors are given:

Examples for central groups:

—NH—CH(OH)—CH(OH)—NH—, —O—, statin, —NH—CH(CH$_2$C$_6$H$_{11}$)—CH(OH)—CH$_2$—NH—, —NH—CH(C$_4$H$_9$)—CO—CH(C$_4$H$_9$)—NH—, —NH—CH$_2$—CH(OH)—CH$_2$—NH—, (1S,3S)-NH—CH(cyclohexylmethyl)-CO—CH(cyclohexylmethyl)—NH—, 2alkylstatin, —CH$_2$—, ethylenepoxide, thiphen Examples for sidechains:

Ac-Ser-Gln-Asn-Tyr- (Ac-SEQ ID NO: 12), H-His-Pro-His-Tyr- (H-SEQ ID NO: 13), Ac-Arg-Ser-Gln-His-Cha- (Ac-SEQ ID NO: 14-CHa-), H-Ala-Ala-

Examples for complete inhibitors:

tBoc-Arg-Ser-Gln-His-NR—CH$_2$—CH(OH)—CH$_2$—NR-His-Gln-Ser-Arg-tBoc (R=—CH$_2$—CH(CH$_3$)$_2$, —CH$_2$—C$_6$H$_{11}$ etc.), H-His-Pro-His-NH—CHR—CH(OH)—CH$_2$—NH-His-Pro-His-H (R=—CH$_2$—C$_6$H$_{11}$ etc.), Ac-His-Pro-His-NH—CHR—CH(OH)—CH$_2$—CO—NH-D-His-D-Gln-OCH$_3$ (R=—CH$_2$—C$_6$H$_{11}$ etc.), Ac-Arg-Ser-Gln-Asn-NH—CH(CH$_2$C$_6$H$_{11}$)—CO—CH (CH$_2$C$_6$H$_{11}$)—NH-Asn-Gln-Ser-Arg-Ac (central groups: 1S,3S; in place of CO also —CH(OH)—, —CO—CO—, —CH(OH)—CH(OH)—CH(OH)—, furan, ethylenepoxide etc.) SEQ ID NO: 15 is Arg-Ser-Gln-Asn tBoc-His-Pro-Phe-His-Leu-statin-D-His-D-Phe-D-Pro-D-His-tBoc SEQ ID NO: 16 is His-Pro-Phe-His-Leu There now follows a short schematic procedure for the inhibition of proteases eg HIV protease via a particular peptide:

1. determine the symmetry of the enzyme to be inhibited,
2. select the sequence of a good substrate or inhibitory peptide,
3. establish the residue nearest the symmetry centre,
4. bind such a peptide via this residue to a central group by chemical synthesis, such that a sufficiently symmetric peptide results,
5. choose a central group such that the corresponding amino acids are at the correct distance from the centre,
6. check for a good fit and that the inhibitor complies with the symmetry requirements through computer aided molecular design,
7. check for inhibition, especially if the structure coordinates are unknown. In this last case, the sequence of the side arms and the structure of the central groups must be optimised by trial and error with respect to the inhibition.

The chemical production of such compounds is established, as are methods for their administration, such that a specialist can begin the process using known methods.

Finally, some preferred implementations of inhibitor compounds are given:

The compounds are composed preferentially of peptides or peptide analogous structures or of compounds containing peptides or peptide analogous structures or deriving from such structures, whereby the following symmetric or piecewise symmetric compounds are taken into consideration: X-Y-Z-M-Z-X-Y, Z-M-Z, X-Y-Z-Z-Y-X, X-Y-Z-M-Z-Y', X-U-Y-X-Z-Z-X-Y'-X, Z-Z-Y-R, R-U-X-Y-Z-M-Z, or simply M, where X, Y, Z, U, R are organic residues, in particular amino acids or their derivatives, monosaccharides or their derivatives, fatty acids or their derivatives, M represents the central organo-chemical group, and the two structures Y either side of the central group are structurally or physicochemically related compounds, which holds additionally or instead for groups X, Z, U or R. Through good fit, a symmetric or nearly symmetric group M may be sufficient for inhibition, eg a dipeptide analogue, such as that shown on page 12, lines 22–24 for the group M from —NH— ... to ... —NH—.

The required binding of the compounds under consideration to the enzyme can be accomplished for example through utilisation of a typical cleavage or binding sequence of the natural substrate or structures related to these, modified in such a way that the compound serves no longer as a substrate but as an inhibitor. This requirement can also be achieved by a substrate or substrate like compound modified in such a way that the site to be modified by the enzyme is occupied by an unmodifiable group, thus acting as an inhibitor.

In the case of proteases as target enzymes, a preferred group of inhibitory compounds have in place of the cleavable peptide bond a dipeptide analogue with a reduced peptide bond, or a related compound with an uncleavable bond and length the same or similar to that of a dipeptide, thus acting as inhibitors of the target enzyme. In the case of proteases as target enzymes, the compounds can have in place of the clearable peptide bond statin or a derivative of statin or a related or similar uncleavable compound with the same or similar length to that of a dipeptide. In the case of proteases as target enzyme, a phosphorus containing uncleavable compound with the same or similar length as a dipeptide, such as eg phosphonic amide, can be put in place of the clearable peptide bond. Statin and similar dipeptide analogues themselves exhibit approximately symmetric compounds (symmetry near to —OH).

With proteases as target enzymes, the introduction of a longer amino acid or organo-chemical group to the inhibitory compound can shift the spatial position of the cleavable peptide bond relative to the cleavage site position in a good substrate, whereby the compound acts as an inhibitor. For example, introducing statin or a related organo-chemical group or other group can shift the spatial position of the cleavable peptide bond with respect to that of a good substrate.

The symmetry or piecewise symmetry of the compounds under consideration can be achieved if the compound possesses a central organo-chemical group that acts as a centre of symmetry or approximate symmetry, or if the compound contains a central organo-chemical group with two identical or functionally equivalent organic substituents which can so react with two identical or piecewise identical peptides or peptide like compounds to form an overall symmetric or piecewise symmetric compound, eg corresponding to the formulae

C-CONH-B-CONH-A-CONH-M-NHCO-A-NHCO-B-NHCO-C or

C-NHCO-B-NHCO-A-NHCO-M-CONH-A-CONH-B-CONH-C where A, B, C represent amino acid residues and M a central organo-chemical group. The compounds can contain a symmetric or approximately symmetric central organo-chemical group of a length equivalent to at least that of a dipeptide with two identical or functionally equivalent organic substituents that can react with peptides or peptide like compounds such that a symmetric or approximately or piecewise symmetric structure results. In the case that the first example formula above ( ... —NH—M—NH— ... ) corresponds to a good inhibitor, then compounds of the second example ( ... —CO—M—CO— ... ) must possess the same amino acids (A, B, C) with reversed chirality ('D' forms) in order to achieve a similarly good fit and thereby inhibition.

For the case where a central organo-chemical group with two unequal substituents has two equal or approximately equal or complementary peptides or peptide like compounds bound, the following formulae serve as examples:

C-CONH-B-CONH-A-CONH-M-CONH-A-CONH-B-CONH-C

C-NHCO-B-NHCO-A-NHCO-M-NHCO-A-NHCO-B-NHCO-C where A, B, C are amino acid residues and M the central organo-chemical group. The symmetric sequence order alone is insufficient for constituting a sufficiently 'symmetric' inhibitor in general, further explained below (see also page 5).

The compounds can also contain two statin residues or two corresponding compounds with or without intermediary groups such that an overall spatially symmetric or approximate or piecewise symmetric compound results, whereby the compounds can contain two statin residues with opposite chirality or two corresponding related compounds with or without intermediary groups. The compounds can contain two statin residues or two corresponding related compounds with or without intermediary groups, whereby one of the statin residues is terminal, guaranteeing the free rotation of the bonds and facilitating achievement of an overall spatially symmetric or piecewise symmetric conformation of the compound.

If, as in the usual case, one part of the peptide chain of the compound is composed of amino acids of a single spatial conformation (eg L-form), then the other half must consist of amino acids of the opposite configuration to produce a sufficiently symmetric inhibitor. The following examples are preferred:

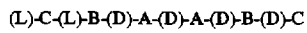

or

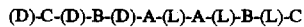

where A, B, C represent amino acids.

In these compounds, a non-peptide residue can be so bonded to a peptide or peptide like compound that an approximately or piecewise symmetric overall structure results, eg regarding one or more physico-chemical properties such as charge, hydrophilicity, hydrophobicity or residue side chain size, or a side chain or non-peptide residue can be bonded to a peptide or peptide like compound or to a peptide with a central organo-chemical group, eg corresponding to the formulae B-A-M-A-R or R-B-A-M-A or R-C-B-A-B-A or B-A-M-R, where A, B, C, D represent amino acid residues, M a central organo-chemical group and R an organic residue, in such a manner that an overall approximate or piecewise symmetric compound results, eg in relation to one or more physico chemical properties such as charge, hydrophilicity, hydrophobicity or residue side chain size.

Chemically reactive residues, eg corresponding to the formulae $XCH_2CO$—, $N_2CHCO$—, NC—$CH_2$—CO—, $RO_2C$—, $CH_2$=CR—, $RO_nS$—, HS—, $RO(H_2N=)C^+$ can be so bound to a symmetric or approximate or piecewise symmetric peptide or peptide like compound, that the compound can bind reversibly or irreversibly to the target enzyme. Here n=1 or 2 and R is an usual ester residue as specified earlier.

The compounds can also contain amino acid sequences of the enzyme or protein that are responsible for the association of their subunits or sub-structures or the stability or structural arrangement of the functional enzyme or protein, or related or similar amino acid sequences or containing structurally similar organo-chemical residues, such that the compounds can adversely affect the structure or stability of the enzyme or protein or its enzymatic activity or impair its function or affect its formation. Hereby, the compounds can contain amino acid sequences of the HIV protease, or related or similar amino acid sequences or structurally similar organo-chemical residues, that are jointly responsible for the association of the enzyme subunits and the formation of the functional enzyme complex, such that the compound can adversely affect the structure or stability of the enzyme complex or reduce its enzymatic activity or prevent its formation.

The compounds can contain preferably the amino acid sequences Trp-Lys-Pro-Lys-Met-Ile-Gly-Gly-Ile-Gly-Gly-Phe-Ile-Lys-Val-Arg; (SEQ ID NO: 17) Gln-Ile-Leu-Ile-Glu-Cys; (SEQ ID NO: 18) Val-Gly-Pro-Thr-Pro-Val-Asn; (SEQ ID NO: 19) Ile-Gly-Arg-Asn; (SEQ ID NO: 6) Ala-Gly-Arg-Asn-Leu-Leu-Thr-Gln-Ile or related (SEQ ID NO: 20) or similar amino acid sequences or structurally similar organo-chemical residues or parts thereof, that are jointly responsible for the association of the subunits of HIV protease and the formation or integrity of the functional enzyme complex, so that the compounds can impair the structure or stability of the enzyme complex or reduce its enzymatic activity or prevent its formation.

In this way, therefore, the structure and/or action of an enzyme of known symmetry, being composed of equal or unequal subunits, in particular enzymes from pathogenic bacteria or viruses, or native enzymes in pathological states, can be inhibited through the use of stable organo-chemical compounds, which can be used for therapy, if the said compounds contain amino acid sequences of the structurally asymmetric complex target enzyme, or structurally similar organo-chemical residues, responsible for the association of the subunits of the enzyme and the integrity of the functional enzyme complex, so that the compounds can perturb the formation or integrity or stability of the enzyme complex and impair or prevent its activity.

TABLE I

Reverse Transkriptase Determination (epm/ml)

| Day post infection | 7 | 8 | 9 | 12 |
|---|---|---|---|---|
| | | | | no inhibitor |
| HIV Control 1 | 12401 | 23708 | 18921 | 165540 |
| HIV Control 2 | 4183 | 30094 | 13680 | 168620 |
| A 1000 µM | 1529 | 2121 | 1550 | 104660 |
| 100 µM | 5378 | 6407 | 12893 | 142240 |
| 10 µM | 4615 | 5381 | 12517 | 117910 |
| 1 µM | 4041 | 7460 | 9502 | 163130 |
| 0,1 µM | 3929 | 6914 | 14455 | 137470 |
| B 1000 µM | 3441 | 3159 | 5503 | 149020 |
| 100 µM | 4033 | 4418 | 6575 | 125290 |
| 10 µM | 4614 | 4188 | 7187 | 164920 |
| 1 µM | 6105 | 3006 | 8474 | 92020 |
| 0,1 µM | 2099 | 3091 | 6180 | 106830 |
| HIV Control 1 | 12401 | 23708 | 18921 | 165540 |
| HIV Control 2 | 4183 | 30054 | 13680 | 168620 |
| C 1000 µM | 7646 | 4308 | 5343 | 107640 |
| 100 µM | 3838 | 6370 | 8860 | 96780 |
| 10 µM | 5358 | 4398 | 8823 | 158800 |
| 1 µM | 4575 | 3198 | 4186 | 164240 |
| 0,1 µM | 5561 | 2314 | 7477 | 113340 |
| D 1000 µM | - Not tested | | | |
| 100 µM | 4393 | 2663 | 3022 | 1533 |
| 10 µM | 4112 | 5411 | 2914 | 210720 |
| 1 µM | 6777 | 2058 | 2227 | 213750 |
| 0,1 µM | 5550 | 3844 | 2304 | 139610 |
| HIV Control 1 | 12401 | 23708 | 18921 | 165540 |
| HIV Control 2 | 4183 | 30094 | 13680 | 168620 |
| 100 µM | 3099 | 3709 | 10344 | 97040 |
| 10 µM | 4537 | 5825 | 4340 | 153830 |
| 1 µM | 3155 | 1663 | 6595 | 201520 |
| 0,1 µM | 5487 | 982 | 2994 | 149330 |
| 100 µM | 3770 | 5958 | 6656 | 129730 |
| 10 µM | 4854 | 8069 | — | 164570 |
| 1 µM | 2955 | 7606 | 3925 | 122840 |
| 0,1 µM | 3328 | 5959 | 4279 | 93946 |

Conclusion: All substances tested showed a significant inhibitory effect on HIV-1 replication as measured by total antigen production or by reverse transcriptase measurement of released virus. This effect was reversible as virus production quickly returned to control levels after removal of inhibitor from infected cells.

TABLE II

Results: HIV-1 antigen production as measured in antigen capture ELISA, values are o. D. H 9 cells readings.

| Day post infection | 1 | 2 | 3 | 4 | 5 | 6 | 7 | 8 | 9 | 12 |
|---|---|---|---|---|---|---|---|---|---|---|
| | | | | | | | | | no inhibitor | |
| HIV Control 1 | 0,075 | 0,059 | 0,068 | 0,059 | 0,080 | 0,182 | 0,811 | 0,748 | 1,052 | 1,017 |
| HIV Control 2 | 0,074 | 0,062 | 0,063 | 0,059 | 0,053 | 0,115 | 0,498 | 0,698 | 1,038 | 1,048 |
| A 1000 µM | 0,087 | 0,058 | 0,073 | 0,054 | 0,056 | 0,102 | 0,286 | 0,597 | 0,899 | 1,054 |
| 100 µM | 0,068 | 0,064 | 0,065 | 0,053 | 0,057 | 0,070 | 0,361 | 0,374 | 0,915 | 1,013 |
| 10 µM | 0,061 | 0,075 | 0,069 | 0,044 | 0,064 | 0,140 | 0,256 | 0,499 | 0,727 | 1,003 |
| 1 µM | 0,064 | 0,060 | 0,075 | 0,057 | 0,053 | 0,136 | 0,213 | 0,394 | 0,694 | 1,065 |
| 0,1 µM | 0,060 | 0,066 | 0,062 | 0,055 | 0,058 | 0,181 | 0,363 | 0,478 | 0,737 | 1,037 |
| B 1000 µM | 0,076 | 0,068 | 0,050 | 0,050 | 0,063 | 0,075 | 0,279 | 0,577 | 0,811 | 1,050 |
| 100 µM | 0,068 | 0,070 | 0,063 | 0,052 | 0,052 | 0,099 | 0,359 | 0,260 | 0,890 | 0,960 |
| 10 µM | 0,063 | 0,060 | 0,059 | 0,047 | 0,055 | 0,087 | 0,303 | 0,342 | 0,645 | 1,038 |
| 1 µM | 0,063 | 0,060 | 0,061 | 0,050 | 0,052 | 0,105 | 0,186 | 0,237 | 0,745 | 0,970 |
| 0,1 µM | 0,061 | 0,063 | 0,039 | 0,063 | 0,055 | 0,149 | 0,389 | 0,232 | 0,700 | 1,047 |
| C 1000 µM | 0,071 | 0,053 | 0,061 | 0,057 | 0,123 | 0,096 | 0,415 | 0,778 | 1,019 | 1,000 |
| 100 µM | 0,064 | 0,056 | 0,062 | 0,053 | 0,061 | 0,100 | 0,265 | 0,296 | 0,787 | 0,940 |
| 10 µM | 0,069 | 0,048 | 0,066 | 0,064 | 0,049 | 0,099 | 0,228 | 0,292 | 0,643 | 1,040 |
| 1 µM | 0,061 | 0,054 | 0,060 | 0,050 | 0,051 | 0,133 | 0,267 | 0,239 | 0,808 | 1,042 |
| 0,1 µM | 0,062 | 0,069 | 0,055 | 0,052 | 0,054 | 0,105 | 0,276 | 0,336 | 0,588 | 1,010 |
| D 1000 µM | - not tested | | | | | | | | | |
| 100 µM | 0,067 | 0,032 | 0,064 | 0,060 | 0,059 | 0,079 | 0,175 | 0,369 | 0,412 | 0,278 |
| 10 µM | 0,068 | 0,066 | 0,072 | 0,060 | 0,059 | 0,081 | 0,218 | 0,368 | 0,886 | 0,975 |
| 1 µM | 0,064 | 0,057 | 0,055 | 0,044 | 0,053 | 0,108 | 0,244 | 0,465 | 0,854 | 1,031 |
| 0,1 µM | 0,057 | 0,055 | 0,051 | 0,054 | 0,057 | 0,134 | 0,380 | 0,366 | 0,906 | 0,996 |
| 100 µM | 0,065 | 0,063 | 0,058 | 0,052 | 0,062 | 0,084 | 0,258 | 0,268 | 0,626 | 1,050 |
| 10 µM | 0,065 | 0,066 | 0,064 | 0,050 | 0,058 | 0,107 | 0,308 | 0,308 | 0,738 | 1,059 |
| 1 µM | 0,066 | 0,056 | 0,069 | 0,055 | 0,059 | 0,124 | 0,458 | 0,464 | 0,807 | 1,028 |
| 0,1 µM | 0,058 | 0,064 | 0,045 | 0,043 | 0,053 | 0,115 | 0,266 | 0,525 | 0,870 | 1,002 |
| 100 µM | 0,064 | 0,059 | 0,069 | 0,056 | 0,056 | 0,100 | 0,407 | 0,547 | 0,924 | 1,060 |
| 10 µM | 0,065 | 0,026 | 0,062 | 0,061 | 0,059 | 0,127 | 0,336 | 0,439 | — | 1,001 |
| 1 µM | 0,067 | 0,061 | 0,068 | 0,051 | 0,058 | 0,149 | 0,354 | 0,367 | 0,891 | 1,020 |
| 0,1 µM | 0,060 | 0,057 | 0,063 | 0,046 | 0,050 | 0,121 | 0,464 | 0,434 | 0,984 | 1,066 |

We claim:

1. A substance for the inhibition of HIV protease which has the formula Y-M-Z, wherein M is —NH—CO—CH($C_4H_9$)—CO—, when Y is acetyl-(D)-Arg-(D)-Ala-(D)-Gln-(D)-Leu- and Z is -(L)-Gln-(L)-Ala-(L)-Arg-$NH_2$;

M is —NH—$CH_2$—CH($C_3H_7$)—CO—, when Y is acetyl-(L)-Arg-(L)-Ala-(L)-Asn-(L)-Leu- and Z is -(D)-Asn-(D)-Gln-(D)-Leu-$NH_2$;

M is —NH—$CH_2$—CO—$CH_2$—CO—, when Y is acetyl-(D)-Arg-(D)-Ala-(D)-Gln- and Z is -(L)-Gln-(L)-Ala-(L)-Arg-$NH_2$;

M is -statin-, when Y is acetyl-(D)-Arg-(D)-Ala-(D)-Asn- and Z is -(L)-Asn-(L)-Ala-(L)-Arg-$NH_2$;

M is -statin-, when Y is acetyl-(L)-Arg-(L)-Ala-(L)-Gln- and Z is -(D)-Gln-(D)-Ala-(D)-Arg-OH;

M is -statin-, when Y is fluoroacetyl-(L)-Arg-(L)-Ala-(L)-Asn- and Z is -(D)-Asn-(D)-Ala-(D)-Arg-$NH_2$;

M is -statin-, when Y is acetyl-(D)-Arg-(D)-Ala-(D)-Leu- and Z is -(L)-Leu-(L)-Ala-(L)-Arg-$NH_2$;

M is —NH—$CH_2$—CH(OH)—$CH_2$—CO—, when Y is acetyl-(D)-Leu-(D)-Arg-(D)-Asn- and Z is -(L)-Asn-(L)-Arg-(L)-Leu-$NH_2$;

M is —NH—$(CH_2)_3$—NH, NH—$CH_2$—O—$CH_2$—NH—, —NH—$CH_2$—CHOH—$CH_2$—NH—, or —NH—$CH_2$—NH—$CH_2$—$NCH_3$—, when Y is acetyl-Arg-Leu-Asn- and Z is -Asn-Leu-Arg-acetyl;

M is —NH—CHF—CO—CHF—NH—, when Y is H-(D)-Leu-(D)-Leu-(D)-Asn- and Z is -(D)-Asn-(D)-Leu-(D)-Arg-H; and further M groups which may be used with any combination of the above Y and Z groups are:

—S—S—, —S—, —O—,

—CO—CHR—CH(OH)—CHR'—CO—, —NR—NR'—,

—NH—CHR—CH(OH)—CHR'—NH—, —NH—$CF_2$—CO—$CH_2$—NH—,

—NH—$CF_2$—CO—$CF_2$—NH—, —CO—$(CH_2)_3$—CO—,

—NH—$(CH_2)_3$—NH—, —CO—$CH_2$—O—$CH_2$—CO—, —N(OR)—, —NR—,

—P(O)$_n$OH—, —CO—CHR—CO—,

—NH—$CH_2$—O—$CH_2$—NH—, —CO—$CH_2$—NR—$CH_2$—CO—,

—N($C_5H_{11}$)—$CF_2$—CO—$CF_2$—N($C_5H_{11}$)—,

N($C_4H_9$)—$CH_2$—CH(OH)—$CH_2$—N($C_4H_9$)—, and

-(2S,3S)-NH—CH($CH_2C_6H_{11}$)—CH(OH)—$CH_2$—NR—, where R and R' are hydrogen or $C_{1-12}$ aryl- or alkyl-groups and n is 1 or 2.

2. The substance of claim 1 where Y is acetyl-Arg-Leu-Asn and Z is Asn-Leu-Arg-acetyl or Y is H-(D)-Leu-(D)-Leu-(D)-Asn- and Z is -(D)-Asn-(D)-Leu-(D)-Arg-H.

3. The substance of claim 2 wherein M is —NH—$(CH_2)_3$—NH—, —NH—$CH_2$—O—$CH_2$—NH— or NH—$CH_2$CHOH—$CH_2$—NH—.

4. The substance of claim 2 having the formula acetyl-Arg-Leu-Asn-NH—CHR—CH(OH)—CHR'—NH-Asn-Leu-Arg-acetyl, where R and R' are hydrogen or $C_{1-12}$ aryl- or alkyl-groups.

* * * * *